United States Patent
Zawierucha et al.

(10) Patent No.: US 9,060,516 B2
(45) Date of Patent: Jun. 23, 2015

(54) METHOD FOR CONTROLLING AQUATIC WEEDS

(75) Inventors: Joseph Zawierucha, Cary, NC (US);
Glenn W. Oliver, Apex, NC (US);
Richard R. Evans, Raleigh, NC (US);
Todd Horton, Anderson, SC (US);
Daniel D. Beran, Des Moines, IA (US);
Joseph G. Vollmer, Laramie, WY (US);
Alane J-Bo Burns, Raleigh, NC (US);
Jeffrey H. Birk, Raleigh, NC (US);
Derek W. Miller, Apex, NC (US);
Timothy P. Knight, Raleigh, NC (US)

(73) Assignee: BASF SE, Ludwigshafen (DE)

(*) Notice: Subject to any disclaimer, the term of this patent is extended or adjusted under 35 U.S.C. 154(b) by 1289 days.

(21) Appl. No.: 12/158,227

(22) PCT Filed: Dec. 20, 2006

(86) PCT No.: PCT/EP2006/070009
§ 371 (c)(1),
(2), (4) Date: Sep. 25, 2008

(87) PCT Pub. No.: WO2007/071730
PCT Pub. Date: Jun. 28, 2007

(65) Prior Publication Data
US 2009/0011934 A1 Jan. 8, 2009

Related U.S. Application Data

(60) Provisional application No. 60/752,906, filed on Dec. 23, 2005, provisional application No. 60/802,791, filed on May 24, 2006.

(51) Int. Cl.
*A01N 59/00* (2006.01)
*A01N 43/34* (2006.01)
*A01N 43/42* (2006.01)

(52) U.S. Cl.
CPC ..................... *A01N 43/42* (2013.01)

(58) Field of Classification Search
None
See application file for complete search history.

(56) References Cited

U.S. PATENT DOCUMENTS

| | | | |
|---|---|---|---|
| 4,398,937 A | 8/1983 | van Aller et al. | |
| 4,497,651 A | 2/1985 | Hagen et al. | |
| 4,632,696 A | 12/1986 | Hagen et al. | |
| 4,715,889 A | 12/1987 | Hagen et al. | |
| 4,798,619 A | 1/1989 | Los | |
| 5,334,576 A | 8/1994 | Doehner, Jr. et al. | |
| 5,973,154 A | 10/1999 | Drabb et al. | |
| 6,339,158 B1 | 1/2002 | Wepplo et al. | |
| 6,677,276 B1 | 1/2004 | Hacker et al. | |

| | | | |
|---|---|---|---|
| 2002/0119891 A1 | 8/2002 | Netherland | |
| 2003/0186815 A1 | 10/2003 | Hacker et al. | |
| 2008/0305954 A1 | 12/2008 | Zawierucha et al. | |

FOREIGN PATENT DOCUMENTS

| | | |
|---|---|---|
| CN | 1401232 | 3/2003 |
| EP | 0 094 181 | 11/1983 |
| EP | 0 127 433 | 12/1984 |
| WO | WO 2005/077169 | 8/2005 |
| WO | WO 2005/096814 | 10/2005 |
| WO | WO 2007/014758 | 2/2007 |
| WO | WO 2007/014760 | 2/2007 |
| WO | WO 2007/014761 | 2/2007 |
| WO | WO 2007/042447 | 4/2007 |
| WO | WO 2007/071655 | 6/2007 |

OTHER PUBLICATIONS

Tanaka et al. (Evaluation of herbicides for the control of egeria laboratory water box and dam without water flow, Plant Weed vol. 20, p. 73-81, 2002).*
Capers et al. (Invasive Aquatic Plants, Connecticut Agricultural Experiment Station, Bulletin No. 997, Jan. 2005).*
Michel et al. (Somatic mutation-mediated evolution of herbicide resistance in the nonindigenous invasive plant hydrilla, Molecular Ecology, vol. 13, 2004, pg. 3229-3237).*
Nelson et al. (Response of Wild Rice to Selected Aquatic Herbicides, U.S. Army Corps of Engineers, Sep. 2003).*
Hoyer, M.V., et al., "Hydrilla Management in Florida: A Summary and Discussion of Issues Identified by Professinals with Future Management recommendations", University of Florida Department of Fisheries and Aquatic Sciences, Jun. 2005, pp. 1-22.
International Preliminary Report on Patentability issued Jun. 24, 2008, from corresponding International Application No. PCT/EP2006/070009, filed Dec. 20, 2006.

(Continued)

*Primary Examiner* — Rebecca Prouty
*Assistant Examiner* — Danielle Sullivan
(74) *Attorney, Agent, or Firm* — Brinks Gilson & Lione

(57) ABSTRACT

The present invention relates to a method for the control of aquatic weeds which comprises applying a herbicidally effective amount of at least one compound of formula (I)

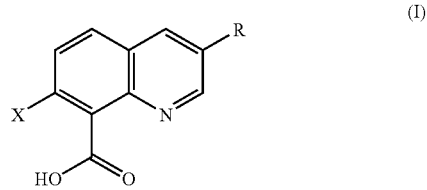

(I)

wherein
X is halogen and
R is halogen or $C_1$-$C_6$ alkyl,
and/or one or more agriculturally acceptable salts thereof to act on submersed aquatic weeds and/or their aqueous habitat containing seeds or other propagating organs of said aquatic weeds.

10 Claims, No Drawings

(56) References Cited

OTHER PUBLICATIONS

International Search Report completed Jan. 16, 2008, in International Application No. PCT/EP2006/070009, filed Dec. 20, 2006.

Anderson, L.W.J, "A review of aquatic weed biology and management research conducted by the United States Department of Agriculture—Agricultural Research Services", Pest Manag. Sci., 2003, pp. 801-813, vol. 59.

Anderson, Lars, W.J., "Movement of 14-C Arsenal® (imazapyr) into monoecious *Hydrilla verticillata* tubers", Res Prog. Rep. West. Soc. Weed Sci, 1986 Meeting, p. 304.

Arias, Renee S., et al., "Molecular evolution of herbicides resistance to phytoene desaturase inhibitors in *Hydrilla verticillata* and its potential use to generate herbicide-resistant crops" Pest Manag Sci, 2005, p. 258-268, vol. 61.

Beck, J., et al., "Quinclorac (BAS 514) and its Herbicide-Combinations in Transplanted Rice in Japan" Proc. 12th Conf. of Asia-Pacific Weed Science Society, 1989, p. 235-244.

Braverman, M.P. et al., "Weed Control in Rice (*Oryza sativa*) with Quinclorac and Bensulfuron Coating of Granular Herbicides and Fertilizer" Weed Technology, 1995, p. 494-498, vol. 9.

Database CA [Online] Chemical Abstracts Service, Columbus, Ohio, US; XP002464636 retrieved from STN-International Database accession No. 141:84041.

Gallagher, J. et al., "History and Development of Aquatic Weed Control in the United States", Rev. Weed Sci, 1990, p. 115-195, vol. 5.

Grossman, Klaus, "Quinclorac belongs to a new class of highly selective auxin herbicides", Weed Science, 1998, p. 707-716, vol. 46.

Netherland, M.D., et al., "Aquatic Plant Management: Invasive species and Chemical Control", Outlooks on Pest Management (Pesticide Outlook), Jun. 2005, pp. 100-104, vol. 16, No. 3.

Kay, S. H., et al., "Response Of Two Alligatorweed Biotypes To Quinclorac" Journal of Aquatic Plant Management, Society, Washington, DC US, 1992, pp. 35-40, vol. 30, XP008086947 ISSN: 0146-6623.

Klingman, et al., "Aquatic-Weed Control" Weed Science, Weed Science Society Of America, Champaign, Il, US, 1982, pp. 383-402, XP002962279 ISSN: 0043-1745 p. 389; tables 29-1.

Langeland, K., et al. "Efficacy of Herbicide Active Ingredients Against Aquatic Weeds". Biology and Control of Algae. Agronomy Department Document SS AGR 44, Florida Cooperative Extension Service, Institute of Food and Agricultural Sciences, University of Florida, Gainesville, FL 32611, Sep. 2006, http://www.edis.ifas.ufl.edu/.

Mabbayad, M.O., et al., "Herbicide seed treatment for weed control in wet-seeded rice", Tropical Pest Management, 1992, p. 9-12, vol. 38, No. 1.

Street, J.E., et al., "Rice (*Oryza sativa*) Weed Control With Soil Applications of Quinclorac" Weed Technology, 1993, p. 600-604, vol. 7.

"The e-Pesticide Manual (Thirteenth Edition) Version 3.0" 2003, British Crop Protection Council, XP002464632 entry 712: "Quinclorac".

"The e-Pesticide Manual (Thirteenth Edition) Version 3.0" 2003, British Crop Protection Council, XP002464633 entry 713: "Quinmerac".

"The e-Pesticide Manual (Thirteenth Edition) Version 3.0" 2003, British Crop Protection Council, XP002464634 entry 211: "2,4-D".

Zoschke, A., et al., "CGA142'464 plus BAS-514, a new timing-flexible herbicide combination for broadspectrum weed control in rice (*Oryza sativa* L.) in South Korea", 12th Asian-Pacific Weed Science Society Conference, 1989, pp. 245-253, No. 1. and XP002464635 retrieved from STN-International Database accession No. 91:73631.

Rattray, M.R., et al., "The Mechanism of Action of Bensulfuron-Methyl on Hydrilla", J. Aquatic Plant Manage., 1993, p. 39-42, vol. 31.

\* cited by examiner

METHOD FOR CONTROLLING AQUATIC WEEDS

This application is a National Stage application of International Application No. PCT/EP2006/070009 filed Dec. 20, 2006, which claims the benefit of U.S. Provisional Application Nos. 60/752,905 and 60/802,791, filed Dec. 23, 2005 and May. 24, 2006, respectively, the entire contents of which are hereby incorporated herein by reference.

This invention belongs to the field of agricultural chemistry and provides to the art compounds to control aquatic weeds. Such weeds clog waterways, plug up water-handling equipment, and are often aesthetically unacceptable. They are cumbersome for fisherman, swimmers, and watersports. The economic impact for control and management in general and on recreational areas in particular is estimated to be in the millions of dollars.

A typical representative for inventively controlled aquatic weeds is *hydrilla* that is known as a submersed, very prolific, mat forming species, which can dominate the aquatic system that it is present in. High densities of *hydrilla* interfere with various water uses. A typical representative is *Hydrilla verticillata*.

Therefore, the development of herbicides effective against aquatic weeds is important. The control of certain aquatic weeds is discussed in the following art.

Generally, aquatic weeds and herbicidal or biological methods for controlling them are known, for example from L. W. J. Anderson, Pest Manag. Sci. 59, pages 801-813 (online 2003) or M. D. Netherland et al., Outlooks on Pest Management (Pesticide Outlook), pages 100-104 or J. Gallagher and W. T. Haller, Rev. Weed Sci., 1990, 5, 115-192.

One of the major herbicides used for the control of *Hydrilla verticillata* is fluridone (1-methyl-3-phenyl-5-[3-(trifluoromethyl)phenyl]-4(1H)-pyridinone).

It is known that a number of new biotypes of *hydrilla* have developed increased tolerance or even resistance to fluridone. Therefore, there is a continuous demand to further develop efficient herbicides for controlling aquatic weeds in general. Thus, the need for a herbicide to control *hydrilla*, in particular *Hydrilla verticillata*, specifically their biotypes being tolerant or resistant to fluridone herbicide is warranted.

It has now been found that compounds of formula (I)

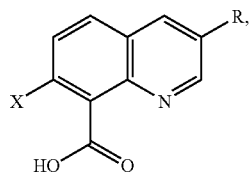

(I)

wherein
  X is halogen and
  R is halogen or $C_1$-$C_6$ alkyl,
and/or agriculturally acceptable salts thereof, optionally in combination with at least one other herbicide, effectively provide growth suppression or control of submersed aquatic weeds in general and of *hydrilla* in particular.

Chinoline derivatives in general, and 3,7-dichloroquinoline-8-carboxylic acid (quinclorac) and 7-chloro-3-methylquinoline-8-carboxylic acid (quinmerac) in particular, are known herbicides, which are described for example in U.S. Pat. Nos. 4,497,651, 4,632,696 and 4,715,889.

Quinclorac is a known herbicide to be used for the protection of grains in general and of rice in particular. The control of weeds in rice is described in a number of publications.

J. Beck, M. Ito, S. Kashibuchi, *Quinclorac (BAS 514) and its Herbicide-Combinations in Transplanted Rice in Japan in: Proc. 12th Conf. of Asia-Pacific Weed Science Society*, 1989, 235-244 describe the control of several weeds which are typically present in paddy rice such as *Echinachloa crusgalli, Cyperus difformis* or *Monochoria vaginalis* by means of quinclorac either as a single herbicide or in combination with several other herbicides.

In J. E. Street, T. C. Mueller, *Rice (Oryza sativa) Weed Control With Soil Applications of Quinclorac in: Weed Technology*, 1993, 7, 600-604 the control of troublesome weeds with regard to rice growth by application to dry or wet soil is described. The weeds under regard have been barnyardgrass (*Echinachloa crus-galli*), pitted morning glory (*Ipomoea lacunose*) and hemp *sesbania* (*Sesbania exaltata*).

The control of a mixture of different weeds in rice by means of e.g. quinclorac or quinclorac and bensulfuron is described by M. O. Mabbayad, K. Moody, *Herbicide seed treatment for weed control in wet-seeded rice in: Tropical Pest Management*, 1992, 38(1), 9-12.

The coating of different kinds of granules with quinclorac is described in M. P. Braverman, *Weed Control in Rice (Oryza sativa) with Quinclorac and Bensulfuron Coating of Granular Herbicides and Fertilizer in: Weed Technology*, 1995, 9, 494-498. The weeds under regard have been ducksalad (*Heteranthera limosa*) and junglerice (*Echinachloa colona*).

It is advantageous if the herbicides also fulfil one or more of the following requirements. The compounds must be effective and efficient.

They should not be harmful to other plants than the ones to be controlled, to animals and man.

They are preferably degradable within a reasonable timeframe and the degradation products are harmless as well.

It is desirable that the compositions comprising the compounds used to control aquatic weeds have a slow activity and, therefore, less oxygen-depleting for the water. On the other hand, it may also be desirable that the compositions have a high activity which allows to eliminate fast-growing aquatic weeds in a short timeframe.

The compositions according to the invention are useful for controlling submersed aquatic weeds. They provide unexpectedly superior control of *hydrilla*. The compounds, therefore, provide a practical and economical method of achieving superior aquatic activity.

The invention therefore provides a method for the control of aquatic weeds which comprises applying a herbicidally effective amount of at least one compound of formula (I)

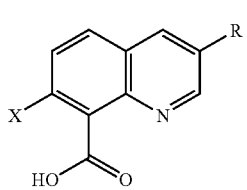

(I)

wherein
  X is halogen and
  R is halogen or $C_1$-$C_6$ alkyl,
and/or one or more agriculturally acceptable salts thereof to act on submersed aquatic weeds and/or their aqueous habitat containing seeds or other propagating organs of said aquatic weeds.

In a further aspect of the invention there is provided the use of a composition comprising a herbicidally effective amount of a compound of formula (I) for controlling submersed aquatic weeds. In yet a further aspect of the invention there is provided a herbicidal composition for controlling submersed aquatic weeds which comprises a herbicidally effective amount of at least one compound of formula (I)

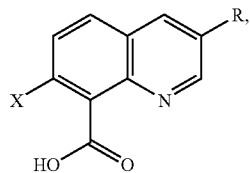

(I)

wherein
X is halogen, and
R is halogen or $C_1$-$C_6$ alkyl,
and/or one or more agriculturally acceptable salts or derivatives thereof.

The term "controlling" in this context means exhibiting aquatic-herbicidal action. This means that the growth of at least one aquatic weed species is reduced or suppressed concerning number and/or size of its plants yielding in e.g. limited growth or death of the weeds.

A weed generally is an unwanted plant. A plant is described as unwanted if its presence is not wanted in a particular place.

Aquatic weeds are unwanted plants that have adapted to living in or on aquatic environments. This includes water as well as water-saturated soil. Thus, their habitat means the living space of the plants including but not limited to water environment like sweet water or salt water sources, either as moving water or still water. Examples thereof are lakes, rivers, streams, wetlands, ponds, creeks, swamps, canals, reservoirs, and ditches. Other examples are marine water environments like oceans, seas, gulfs, and straits. Examples of saturated soils are water-saturated fields, in particular paddy fields.

The symbols in formula (I) are further illustrated in the following.

Halogen denotes fluorine, chlorine, bromine or iodine.

The alkyl moiety mentioned in the definition of radical R and possible salts is a collective term for individual enumerations of the individual group members. The hydrocarbon chain may be straight-chain or branched.

Examples for such meanings are:
$C_1$-$C_4$-alkyl: for example: methyl, ethyl, n-propyl, 1-methylethyl, n-butyl, 1-methylpropyl, 2-methylpropyl and 1,1-dimethylethyl;
$C_1$-$C_6$-alkyl: $C_1$-$C_4$-alkyl as mentioned above and also, for example: n-pentyl, 1-methyl-butyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl.

The alkoxy moiety mentioned in the definition of possible salts is a collective term for individual enumerations of the individual group members. The hydrocarbon chain may be straight-chain or branched.

Examples for such meanings are:
$C_1$-$C_4$-alkoxy: for example: methoxy, ethoxy, n-propoxy, 1-methylethoxy, n-butoxy, 1-methylpropoxy, 2-methylpropoxy and 1,1-dimethylethoxy;
$C_1$-$C_6$-alkoxy: $C_1$-$C_4$-alkoxy as mentioned above and also, for example: n-pentoxy, 1-methyl-butoxy, 2-methyl butoxy, 3-methylbutoxy, 2,2-dimethylpropoxy, 1-ethylpropoxy, n-henoxy, 1,1-dimethylpropoxy, 1,2-dimethylpropoxy, 1-methyl pentoxy, 2-methylpentoxy, 3-methyl pentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethyl butoxy, 2-ethyl butoxy, 1,1,2-trimethylpropoxy, 1-ethyl-1-methylpropoxy and 1-ethyl-3-methylpropoxy.

In a preferred embodiment of the invention X in compound of formula (I) is chlorine.

In a further preferred embodiment R in compound of formula (I) is chlorine or $C_1$ to $C_4$ alkyl.

Particularly preferred R in compound of formula (I) is chlorine or methyl, especially preferred R is chlorine, also especially preferred R is methyl.

Particularly preferred are the compounds where X is chlorine and R is chlorine (quinclorac) and where X is chlorine and R is methyl (quinmerac). Quinclorac is especially preferred. Further, quinmerac is especially preferred.

Aquatic weeds can be further distinguished.

"Emersed aquatic weeds" grow standing out of the water or in water-saturated soil. A typical representative for an emersed species is alligatorweed (*Alternanthera philoxeroides*). Further examples are cattails, bulrushes, and purple loosestrife.

"Submersed aquatic weeds" grow with all or most of their vegetative tissue below the water surface. Typical representatives for submersed species are hydrilla (*Hydrilla*) and milfoil (*Myriophyllum*). Further examples include sego pondweed, southern naiad, *Egeria*, and *Potamogetum*.

"Floating aquatic weeds" float on the water surface. Examples are duckweeds, water-hyacinth, water-lettuce, water-fens, and water-lilies.

"Algae" are considered 'primitive' plants but are often incorporated into the generic group of aquatic weeds.

"Controlling of submersed aquatic weeds" means that at least one submersed aquatic weed is controlled.

When the inventive method (for controlling of submersed aquatic weeds) is applied in the presence of emersed aquatic weeds and/or floating aquatic weeds and/or algae, (simultaneous) controlling of emersed aquatic weeds and/or floating aquatic weeds and/or algae may (also) take place.

A preferred embodiment of the invention comprises a method of using compounds of formula (I), specifically quinclorac, for controlling *hydrilla*, especially preferred *Hydrilla Verticillata*.

The method according to the invention may comprise
(Ia) one or more compounds of formula (I) in the form of the free carboxylic acid or
(Ib) one or more agriculturally acceptable salts of compounds of formula (I) or
(Ic) mixtures comprising two or more compounds chosen from (Ia) and (Ib).

In general, those salts of compounds of formula (I) are suitable, wherein the acidic hydrogen of the carboxylic group is substituted by a cation and the cation has no adverse effect on the action of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di(2-hydroxyeth-1-yl) ammonium, benzyltrimethylammonium, benzyltriethylammonium, furthermore phosphonium ions, sulfonium ions, preferably tri($C_1$-$C_4$-alkyl)sulfonium such as trimethylsulfonium, and sulfoxonium ions, preferably tri($C_1$-$C_4$-alkyl)sulfoxonium.

Another particularly preferred embodiment of the invention comprises a method of using of compound of formula (I) for controlling submersed aquatic weeds wherein the aquatic weeds are tolerant and/or resistant to the herbicide fluridone.

Another particularly preferred embodiment of the invention comprises a method of controlling submersed aquatic weeds which comprises allowing a herbicidally effective amount of compounds of formula (I) and/or one or more agriculturally acceptable salts thereof to act on the submersed aquatic weeds and/or its aqueous habitat containing seeds or other propagating organs of said aquatic weed in the presence of rice plants.

Compounds of formula (I) and/or one or more agriculturally acceptable salts thereof can be used in combination with one or more other herbicide(s) or an agriculturally acceptable salt or derivative thereof.

In the following compounds of formula (I) and/or one or more agriculturally acceptable salts thereof and, where applicable, one or more other herbicide(s) or an agriculturally acceptable salt or derivative thereof will be designated as active compounds.

Examples of such other herbicide(s) are the herbicides (a) selected from the following classes a1) to a15):
a1) lipid biosynthesis inhibitors;
a2) acetolactate synthase inhibitors (ALS inhibitors);
a3) photosynthesis inhibitors;
a4) protoporphyrinogen-IX oxidase inhibitors;
a5) bleacher herbicides;
a6) enolpyruvyl shikimate 3-phosphate synthase inhibitors (EPSP inhibitors);
a7) glutamine synthetase inhibitors;
a8) 7,8-dihydropteroate synthase inhibitors (DHP inhibitors);
a9) mitose inhibitors;
a10) inhibitors of the synthesis of long chain fatty acids (VLCFA inhibitors);
a11) cellulose biosynthesis inhibitors;
a12) decoupler herbicides;
a13) auxin herbicides;
a14) auxin transport inhibitors;
a15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam, methyl bromide, and endothal;
all including the agriculturally acceptable salts and the agriculturally acceptable derivatives thereof (e.g. esters, amides or N-oxides), provided those herbicides have a group that can be derivatized, preferably a carboxyl group, an amino group or a nitrogen atom that can be oxidized, more preferred a carboxyl group.

Preferred herbicides of groups a1) to a15) are the compounds listed below:

a1) from the group of the lipid biosynthesis inhibitors:
chlorazifop, clodinafop, clofop, cyhalofop, diclofop, fenoxaprop, fenoxaprop-p, fenthiaprop, fluazifop, fluazifop-P, haloxyfop, haloxyfop-P, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate, bensulide and pinoxaden;

a2) from the group of the ALS inhibitors:
amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, flucetosulfuron, orthosulfamuron, pyrimisulfan;

a3) from the group of the photosynthesis inhibitors:
atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;

a4) from the group of the protoporphyrinogen-IX oxidase inhibitors:
acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen, etnipromid, and bencarbazone;

a5) from the group of the bleacher herbicides:
metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethyl-phenoxy)-2-(4-trifluoromethylphenyl) pyrimidine, known from EP 723960, topramezone, 4-hydroxy-3-{[2-methyl-6-(trifluoromethyl)-3-pyridinyl]carbonyl}bicyclo[3.2.1]oct-3-en-2-one, known from WO 00/15615, 4-hydroxy-3-{[2-(2-methoxyethoxy)methyl-6-(trifluoro-methyl)-3-pyridinyl] carbonyl}bicylo[3.2.1]oct-3-en-2-one, known from WO 01/94339, 4-hydroxy-3-[4-(methylsulfonyl)-2-nitrobenzoyl]bicyclo[3.2.1]-oct-3-en-2-one, known from EP 338992, 2-[2-chloro-4-(methylsulfonyl)-3-[(2,2,2-trifluoroethoxy)methyl]benzoyl]-3-hydroxy-2-cyclohexen-1-one (known from DE 19846792), and pyrasulfotole;

a6) from the group of the EPSP synthase inhibitors: glyphosate;

a7) from the group of the glutamine synthase inhibitors: glufosinate and bilanaphos;

a8) from the group of the DHP synthase inhibitors: asulam;

a9) from the group of the mitose inhibitors:
benfluralin, butralin, dinitramine, ethalfluralin, fluchloralin, isopropalin, methalpropalin, nitralin, oryzalin, pendamethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

a10) from the group of the VLCFA inhibitors:
acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

a11) from the group of the cellulose biosynthesis inhibitors:
dichlobenil, chlorthiamid, isoxaben and flupoxam;

a12) from the group of the decoupler herbicides:
dinofenate, dinoprop, dinosam, dinoseb, dinoterb, DNOC, etinofen and medinoterb;

a13) from the group of the auxin herbicides:
clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, clopyralid, fluoroxypyr, picloram, triclopyr, benazolin and aminopyralid;

a14) from the group of the auxin transport inhibitors: naptalam, diflufenzopyr;

a15) benzoylprop, flamprop, flamprop-M, bromobutide, chlorflurenol, cinmethylin, methyldymron, etobenzanid, fosamine, metam, pyributicarb, oxaziclomefone, dazomet, triaziflam, methyl bromide, endothal;

all including the agriculturally acceptable salts if the herbicides have functional groups which can be ionised, in particular carboxyl groups, and, provided those herbicides have a group that can be derivatized, preferably a carboxyl group, an amino group or a nitrogen atom that can be oxidized, in particular a carboxyl group, the agriculturally acceptable derivatives of the respective herbicides, preferably esters, amides or N-oxides.

The herbicides of groups a1) to a15) are known herbicides, see the quoted literature references and, for example, The Compendium of Pesticide Common Names (http://www.hclrss.demon.co.uk/index.html); Farm Chemicals Handbook 2000 Vol. 86, Meister Publishing Company, 2000; B. Hock, C. Fedtke, R. R. Schmidt, Herbizide, Georg Thieme Verlag, Stuttgart 1995; W. H. Ahrens, Herbicide Handbook, 7$^{th}$ Edition, Weed Science Society of America, 1994; K. K. Hatzios, Herbicide Handbook, Supplement to 7$^{th}$ Edition, Weed Science Society of America, 1998, and C. D. S. Tomlin, The Pesticide Manual, 13$^{th}$ ed., BCPC, Farnham 2003.

The categorization of the herbicides according to their mode of action is based on current understanding. If a herbicide acts by more than one mode of action, this substance was assigned to only one mode of action.

If the compound (I) and/or one or more agriculturally acceptable salts thereof or the herbicides (a), are capable of forming geometrical isomers, for example E/Z isomers, it is possible to use both the pure isomers and mixtures thereof in the compositions according to the invention.

If the compound (I) and/or one or more agriculturally acceptable salts thereof or the herbicides (a) have one or more centers of chirality and, as a consequence, are pre-sent as enantiomers or diastereomers, it is possible to use both the pure enantiomers and diastereomers and their mixtures in the compositions according to the invention.

If the herbicides (a) are in form of their anionic salts, preferred cations are the same as for the anionic salts of compounds of formula (I).

If the herbicides (a) are in form of their cationic salts, preferred anions are primarily chloride, bromide, fluoride, iodide, hydrogen sulfate, methyl sulfate, sulfate, dihydrogen phosphate, hydrogen phosphate, nitrate, dicarbonate, carbonate, hexafluorosilicate, hexafluorophosphate, benzoate and the anions of $C_1$-$C_4$-alkanoic acids, preferably formate, acetate, propionate and butyrate.

According to the invention, active compounds which carry a group that can be derivatized, preferably a carboxyl group, an amino group or a nitrogen that can be oxidized, in particular a carboxyl group can, instead of the active compounds mentioned above, also be employed in the form of an agriculturally acceptable derivative, for example as amides such as mono- or di-$C_1$-$C_6$-alkylamides or arylamides, as esters, for example as allyl esters, propargyl esters, $C_1$-$C_{10}$-alkyl esters or alkoxyalkyl esters, and also as thioesters, for example as $C_1$-$C_{10}$-alkyl thioesters.

Preferred mono- and di-$C_1$-$C_6$-alkylamides are the methyl- and the dimethylamides. Preferred arylamides are, for example, the anilidines and the 2-chloroanilides. Preferred alkyl esters are, for example, the methyl, ethyl, propyl, isopropyl, butyl, isobutyl, pentyl, mexyl (1-methylhexyl) or isooctyl (2-ethylhexyl) esters. Preferred $C_1$-$C_4$-alkoxy -$C_1$-$C_4$-alkyl esters are the straight-chain or branched $C_1$-$C_4$-alkoxyethyl esters, for example the methoxyethyl, ethoxyethyl or butoxyethyl esters. An example of the straight-chain or branched $C_1$-$C_{10}$-alkyl thioesters is the ethyl thioester.

In binary compositions which comprise compounds of formula (I) and at least one herbicide (a), the weight ratio of the compounds of formula (I):herbicide (a) is usually in the range from 1:500 to 10:1, preferably in the range from 1:100 to 10:1, in particular in the range from 1:50 to 10:1 and particularly preferably in the range from 1:25 to 5:1.

Regarding combinations of compounds of formula (I) and herbicides (a), preference is given to those compositions of the invention which comprise compounds of formula (I) in combination with at least one, preferably exactly one, herbicidally active compound selected from the group consisting of a2) ALS inhibitors, preferably imazapyr and imazomox; a5) bleacher herbicides, preferably fluridone; a13) auxin herbicides; a14) auxin transport inhibitors, preferably diflufenzopyr; and a15) endothal.

Particularly preferred are imazomox and fluridone, especially the combinations quinclorac+imazomox, quinclorac+fluridone, quinmerac+imazomox and quinmerac+fluridone.

For application ready-to-use preparations in the form of crop protection products can be employed. Compounds of formula (I) and optionally one or more herbicide(s) (a) may be present in suspended, emulsified or dissolved form and can be formulated jointly or separately. The application forms depend entirely on the intended use.

The preparations can be applied, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, broadcasting or watering. The use forms depend on the intended use; preferably, they should ensure the finest possible distribution of the active compounds. Coarser distribution might be desired e.g. when a different activity is to be achieved.

Depending on the form in which the ready-to-use preparations are present, they comprise one or more liquid or solid carriers, if appropriate surfactants and if appropriate further auxiliaries which are customary for formulating crop protection products. The person skilled in the art is sufficiently familiar with the recipes for such formulations.

The ready-to-use preparations may comprise auxiliaries, which are customary formulating crop protection products, which auxiliaries may also comprise a liquid carrier.

Suitable inert additives with carrier function are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the active compound(s) as such or dissolved in an oil or solvent, can be homogenized in water by means of wetting agent, tackifier, dispersant or emulsifier. Alternatively, it is possible to prepare concentrates consisting of active compound(s), wetting agent, tackifier, dispersant or emulsifier and, if desired, solvent or oil, and these concentrates are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalene-sulfonic acid, and of fatty acids, of alkyl- and alkylarylsulfonates, of alkyl sulfates, lauryl ether sulfates and fatty alcohol sulfates, and salts of sulfated hexa, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignosulfite waste liquors or methylcellulose.

Powders, materials for spreading and dusts can be prepared by mixing or concomitant grinding of the active compounds with a solid carrier.

Granules, e.g. granules coated by active compound(s), granules impregnated by active compound(s) and granules wherein the active compound(s) are homogenously distributed, can be prepared by binding the active compound(s) to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The binding can be achieved e.g. by means of immersion, spraying or extrusion.

Preferred are liquid formulations and granules, specifically granules, which are preferably applied to the water column with granule applicators mounted on boats.

The concentrations of the active compound(s) in the ready-to-use preparations can be varied within wide ranges. In general, the formulations comprise from 0.001 to 98% by weight, preferably 0.01 to 95% by weight, of active compound(s). The active compound(s) are preferably employed in a purity of from 90% to 100%, preferably 95% to 100% (according to NMR spectrum).

The preparations can, for example, be formulated as follows:

I 20 parts by weight of the active compound(s) in question are dissolved in a composition composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound(s).

II 20 parts by weight of the active compound(s) in question are dissolved in a composition composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound(s).

III 20 parts by weight of the active compound(s) in question are dissolved in a composition composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100 000 parts by weight of water and finely distributing it therein gives an aqueous dispersion which comprises 0.02% by weight of the active compound(s).

IV 20 parts by weight of the active compound(s) in question are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the composition is ground in a hammer mill. Finely distributing the composition in 20 000 parts by weight of water gives a spray composition which comprises 0.1% by weight of the active compound(s).

V 3 parts by weight of the active compound(s) in question are mixed with 97 parts by weight of finely divided kaolin. This gives a dust which comprises 3% by weight of the active compound(s).

VI 20 parts by weight of the active compound(s) in question are mixed intimately with 2 parts by weight of calcium dodecylbenzenesulfonate, 8 parts by weight of fatty alcohol polyglycol ether, 2 parts by weight of the sodium salt of a phenol-urea-formaldehyde condensate and 68 parts by weight of a paraffinic mineral oil. This gives a stable oily dispersion.

VII 1 part by weight of the active compound(s) in question is dissolved in a composition composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the active compound(s) in question is dissolved in a composition composed of 80 parts by weight of cyclohexanone and 20 parts by weight of nonionic emulsifier based on ethoxylated castor oil (Wettol® EM 31, BASF AG). This gives a stable emulsion concentrate.

The compounds of formula (I) and/or one or more agriculturally acceptable salts thereof and/or herbicide(s) (a) can be formulated jointly or separately.

The compounds of formula (I) and/or one or more agriculturally acceptable salts thereof and/or herbicide(s) (a) can be applied jointly or separately, simultaneously or successively, before, during or after appearance of the aquatic weeds.

The required application rate of the pure compounds (I) and/or one or more agriculturally acceptable salts thereof, optionally in combination with a further herbicide (a) without formulation auxiliary, depends on the density of the undesired vegetation, on the development stage of the plants, on the water-movement, on the climatic conditions of the location where the composition is used and on the application method. In general, the application rate is from 1 to 1000 ppb (parts per billion), preferably from 10 to 500 ppb and in particular from 250 to 500 ppb of active compound(s).

The preparations are applied to the water body as either a surface or subsurface application. Application can be carried out by customary spraying techniques using, for example, water as carrier and spray liquid rates of from about 50 to 1 000 l/ha (for example from 300 to 400 l/ha). Application of the preparations by the low-volume and the ultra-low-volume method is possible. In both methods small droplets with a high solids content are formed and dispensed by means of a highly pressurized gas stream. Also possible is the application of the preparations in the form of microgranules.

When applying compounds of formula (I) and/or one or more agriculturally acceptable salts thereof by the method according to this invention the aquatic weeds in general are controlled slowly, meaning the biomass of the aquatic weeds in aqueous systems, for example ponds, lakes, creeks, rivers or swamps is declining slowly and gradually. This is a big advantage compared to other herbicides for control of the aquatic weeds—for example the herbicide endothall—which is also used in controlling the aquatic weeds and which exhibits very rapid, contact control of the aquatic weeds. Rapid, contact biomass reduction under high infestation levels is in general undesirable in that it for example can lead to rapid oxygen depletion in the aqueous system, which then may lead for example to significant fish mortality.

For a more clear understanding of the invention, specific examples are set forth below. These examples are merely illustrations and are not to be understood as limiting the scope and underlying principles of the invention in any way. Various modifications of the invention in addition to those shown and described herein will become apparent to those skilled in the art from the following examples and foregoing description. Such modifications are also intended to fall within the scope of the appended claims.

EXAMPLES

Experiment 1

A Greenhouse Test was Initiated to Evaluate the Effects of Quinclorac for the control of *Hydrilla verticillata*

Materials and Methods:

To begin the experiment, PVC cylinders were filled and maintained with a volume of 4000 ml of dichlorinated water that was maintained at room temperature (24° C.). To each cylinder, an established *hydrilla* plant (potted in sand mixture) was transferred into the water column. *Hydrilla* plants were selected for uniformity and length of shoot growth (approx 15 cm). Plants were allowed to equilibrate in the columns for 24 hrs prior to herbicide treatment. Experimental treatments included an untreated control, and quinclorac at 50, 250 and 500 ppb of actual acid equivalent of herbicide. Treatments were applied to water columns by the use of a pipette. Amount of herbicide applied was based on the total volume of the cylinders (4000 ml). After initial herbicide treatment, the water columns were gently stirred to ensure uniform distribution. Treatments were arranged as a completely random design with 3 replications. Each cylinder was considered the experimental unit. Greenhouse conditions were maintained at 24/18° C. (day/night) cycle for the duration of the experiment. Natural day length was supplemented with halogen lighting to provide a 14 hr photoperiod. Water level in the cylinders was periodically checked and maintained at the 4000 ml level for the duration of the study. After 11 weeks of exposure, *hydrilla* shoot lengths were measured to ascertain herbicide effects.

The results are presented in Table 1.

TABLE 1

Response of *Hydrilla verticillata* to static exposure of quinclorac herbicide at 11 weeks after treatment (WAT).

| Treatment | Rate (ppb) | Hydrilla Shoot Length (cm) |
|---|---|---|
| Control | — | 30.4 |
| Quinclorac | 50 | 15.0 |
| Quinclorac | 250 | 8.9 |
| Quinclorac | 500 | 6.5 |
| LSD at 0.05 | | 11.5 |

Results showed that after the exposure period, quinclorac had a significant effect on the growth of *hydrilla*. In addition to the growth suppression, visual symptomology included reduction in plant vigour and auxinic-like twisting of leaf tissue. Intensity of symptoms tended to be rate responsive.

Experiment 2

A Greenhouse Test was Initiated to Evaluate the Effects of Quinmerac and Quinclorac for the Control of a Mixed Population of Submersed Weed Species: *Hydrilla verticillata* and *Egeria densa*

Materials and Methods:

To begin the experiment, containers were filled and maintained with a volume of 4000 ml of distilled water that was maintained at room temperature (24° C.). To each container, established weed plants (potted in sand mixture) were transferred into the water column. Plants were selected for uniformity and length of shoot growth (approx 15 cm). Plants were allowed to equilibrate in the containers for 24 hrs prior to herbicide treatment. Experimental treatments included an untreated control, quinmerac at 100, 250, and 500 ppb, as well as, quinclorac at 250 ppb of actual acid equivalent of herbicide. Treatments were applied to water columns by the use of a pipette. Amount of herbicide applied was based on the total volume of the containers (4000 ml). After initial herbicide treatment, the water columns were gently stirred to ensure uniform distribution. Treatments were arranged as a completely random design with 3 replications. Each container was considered the experimental unit. Greenhouse conditions were maintained at 24/18° C. (day/night) cycle for the duration of the experiment. Natural day length was supplemented with halogen lighting to provide a 14 hr photoperiod. Water level in the containers was periodically checked and maintained at the 4000 ml level for the duration of the study. After 12 weeks of exposure, weed shoot length and fresh weights were measured to ascertain herbicide effects.

The results are presented in Table 2.

TABLE 2

Response of submersed weeds to static exposure of quinmerac and quinclorac herbicides at 12 weeks after treatment (WAT).

| Treatment | Rate (ppb) | Shoot Length (cm) | Shoot Fresh (grams) |
|---|---|---|---|
| Control | — | 37.3 | 6.8 |
| Quinmerac | 100 | 15.0 | 5.1 |
| Quinmerac | 250 | 8.9 | 0.5 |
| Quinmerac | 500 | 6.5 | 0.1 |
| Quinclorac | 250 | 15.7 | 1.5 |
| LSD at 0.05 | | 17.4 | 3.1 |

Results showed that after the exposure period, that there was a rate response observed with quinmerac on both weed shoot length and fresh weight. Significant reduction in both shoot length and fresh weight vs. the control was observed at the 250 and 500 ppb rates of quinmerac, as well as the 250 ppb rate of quinclorac. In addition to the growth suppression, visual symptomology included reduction in plant vigour and auxinic-like twisting of leaf tissue, which was similar to that observed with quinclorac. Intensity of symptoms tended to be rate responsive.

The invention claimed is:

1. A method for controlling aquatic weeds which comprises applying a herbicidally effective amount of from 1 to 1000 ppb of at least one compound of formula (I)

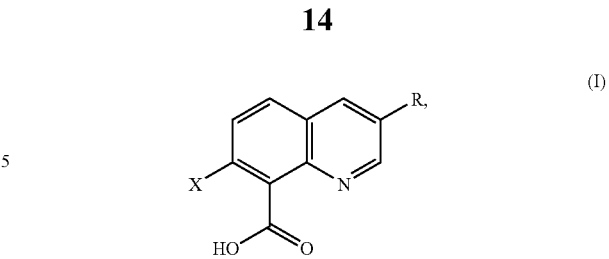

wherein
X is halogen and
R is halogen or $C_1$-$C_6$ alkyl,
and/or one or more agriculturally acceptable salts thereof to submersed aquatic weeds and/or their aqueous habitat containing seeds or other propagating organs of said aquatic weeds, where the compound of formula (I) is applied to the water body as either a surface or subsurface application, wherein aquatic weeds are selected from the genus of *milfoil* and the genus of *hydrilla*.

2. The method according to claim 1, wherein aquatic weeds are selected from the genus of *hydrilla*.

3. The method according to claim 1, wherein X is Cl.

4. The method according to claim 1, wherein R is Cl or $C_1$-$C_4$ alkyl.

5. The method according to claim 1, wherein the aquatic weeds are tolerant and/or resistant to the herbicide fluridone.

6. The method according to claim 1 conducted in the presence of rice plants.

7. The method according to claim 1, wherein a herbicidally effective amount of compounds of formula (I) and/or one or more agriculturally acceptable salts thereof are used in combination with at least one other herbicide.

8. The method according to claim 7, wherein the at least one other herbicide (a) is selected from the following classes a1) to a15):
 a1) lipid biosynthesis inhibitors;
 a2) acetolactate synthase inhibitors (ALS inhibitors);
 a3) photosynthesis inhibitors;
 a4) protoporphyrinogen-IX oxidase inhibitors;
 a5) bleacher herbicides;
 a6) enolpyruvyl shikimate 3-phosphate synthase inhibitors (EPSP inhibitors);
 a7) glutamine synthase inhibitors;
 a8) 7,8-dihydropteroate synthase inhibitors (DHP inhibitors);
 a9) mitose inhibitors;
 a10) inhibitors of the synthesis of long chain fatty acids (VLCFA inhibitors);
 a11) cellulose biosynthesis inhibitors;
 a12) decoupler herbicides;
 a13) auxin herbicides;
 a14) auxin transport inhibitors;
 a15) other herbicides selected from the group consisting of benzoylprop, flamprop, flamprop-M, bromobutide, chlorflurenol, cinmethylin, methyldymuron, etobenzanid, fosamine, metam, pyributicarb, oxaziclomefone, dazomet, triaziflam methyl bromide, and endothal;
all including the agriculturally acceptable salts and the agriculturally acceptable derivatives thereof, provided those herbicides have a carboxyl group.

9. A method for controlling submersed aquatic weeds which comprises applying a herbicidally effective amount of quinclorac or one or more agriculturally acceptable salts thereof to submersed aquatic weeds and/or their aqueous habitat containing seeds or other propagating organs of said aquatic weeds, wherein quinclorac is applied in at an application rate of 500 ppb or less in a body of water and the submersed aquatic weeds include *milfoil*.

10. A method for controlling submersed aquatic weeds which comprises applying a herbicidally effective amount of quinclorac or one or more agriculturally acceptable salts thereof to submersed aquatic weeds and/or their aqueous habitat containing seeds or other propagating organs of said aquatic weeds wherein quinclorac is applied in at an application rate of 500 ppb or less in a body of water and the submersed aquatic weeds include *hydrilla*.

* * * * *